United States Patent
Hamamah

(10) Patent No.: US 9,481,863 B2
(45) Date of Patent: Nov. 1, 2016

(54) METHODS FOR DETERMINING DEVELOPMENTAL STAGE OF HUMAN CUMULUS CELLS

(75) Inventor: Samir Hamamah, Montpellier (FR)

(73) Assignees: INSERM (Institut National de la Santé et de la Recherche Médicale), Paris (FR); CENTRE HOSPITALIER UNIVERSITAIRE DE MONTPELLIER, Montpellier (FR); UNIVERSITE DE MONTPELLIER 1, Montpellier (FR)

( * ) Notice: Subject to any disclaimer, the term of this patent is extended or adjusted under 35 U.S.C. 154(b) by 216 days.

(21) Appl. No.: 14/128,946

(22) PCT Filed: Jun. 29, 2012

(86) PCT No.: PCT/EP2012/062686
§ 371 (c)(1),
(2), (4) Date: Dec. 23, 2013

(87) PCT Pub. No.: WO2013/004612
PCT Pub. Date: Jan. 10, 2013

(65) Prior Publication Data
US 2014/0134632 A1 May 15, 2014

Related U.S. Application Data

(60) Provisional application No. 61/503,684, filed on Jul. 1, 2011.

(30) Foreign Application Priority Data

Jul. 13, 2011 (EP) ..................................... 11305918

(51) Int. Cl.
*C12Q 1/68* (2006.01)
*C12N 5/071* (2010.01)
*C12N 5/073* (2010.01)
*C12N 5/075* (2010.01)

(52) U.S. Cl.
CPC ........... *C12N 5/0605* (2013.01); *C12N 5/0682* (2013.01); *C12Q 1/6881* (2013.01); *C12N 2501/115* (2013.01); *C12N 2533/54* (2013.01)

(58) Field of Classification Search
None
See application file for complete search history.

(56) References Cited

FOREIGN PATENT DOCUMENTS

WO 2010/118991 A1 12/2010

OTHER PUBLICATIONS

Ouandaogo et al., "Specific gene expression in human cumulus cells according to oocyte nuclear maturation stages under in vivo maturation: clinical applications" 25(Suppl. 1) Human Reproduction i 204 (Jun. 2010).*
Assou S, et al., "A non-invasive test for assessing embryo potential by gene expression profiles of human cumulus cells: a proof of concept study", Molecular Human Reproduction, Dec. 1, 2008, pp. 711-719, vol. 14, No. 12, Oxford University Press, GB-BE.
Singh G., et al, "Development of In-Vitro Matured and Fertilized Ovine Oocytes in Conditioned Media Obtained from a Transformed Bovine Fetal Oviductal Epithelial Cell Line Toe136", Theriogenology, Jan. 1992, p. 299, vol. 37, No. 1.
Demilly E., et al., "A novel immortalized human cumulus cells lines with capacity to support human embryonic stem cells growthing: clinical application", Human Reproduction (Oxford), Jul. 2011, pp. I177-I178, vol. 26, No. Suppl. 1.
Goovaerts I. G. F., et al., "Effect of cumulus cell coculture and oxygen tension on the in vitro developmental competence of bovine zygotes cultured singly", Theriogeneology, Mar. 2009, pp. 729-738, vol. 71, No. 5.
Ouandaogo Z. G., et al., "Molecular Signature of human cumulus cells: comparison between in vivo and in vitro maturation conditions", Human Reproduction (Oxford), Jul. 2011, pp. I87-I88, vol. 26, No. Suppl. 1.
Assou S, et al., " Human cumulus cells as biomarkers for embryo and pregnancy outcomes", Molecular Human Reproduction, Aug. 1, 2010, pp. 531-538, vol. 16, No. 8, Oxford University Press, GB-BE.

\* cited by examiner

*Primary Examiner* — Nancy J Leith
(74) *Attorney, Agent, or Firm* — Whitham, Curtis & Cook, P.C.

(57) ABSTRACT

The present invention relates generally to the fields of reproductive medicine. More specifically, the present invention relates to a method determining the developmental stage of human cumulus cells issues from MII oocyte.

2 Claims, 3 Drawing Sheets

METHODS FOR DETERMINING DEVELOPMENTAL STAGE OF HUMAN CUMULUS CELLS

FIELD OF THE INVENTION

The present invention relates generally to the fields of reproductive medicine. More specifically, the present invention relates to a method determining the developmental stage of human cumulus cells issues from MII oocyte.

BACKGROUND OF THE INVENTION

The bidirectional exchanges between oocyte and contiguous cumulus cells (CCs) are important for oocyte competence acquisition, early embryonic development and CC expansion (Cha and Chian, 1998; Goud et al., 1998; Salustri et al., 1989). Oocyte maturation starts with the resumption of the first meiosis process, and is divided in nuclear and cytoplasmic maturation. During nuclear maturation, there is progression from prophase I characterized by germinal vesicle breakdown (GVBD) to metaphase II (MII) of the second meiosis (Cha and Chian, 1998; Wang and Sun, 2007). At the end of this process, the oocyte should be considered as mature and able to be fertilized.

However, the main problem, which hinders in vitro fertilization (IVF) and intracytoplasmic sperm injection (ICSI) success, is how to select oocytes competent for embryonic development and implantation. Gene expression profile of CCs has been suggested to predict embryo development and pregnancy outcome (Adriaenssens et al., 2010; Assou et al., 2008; Assou et al., 2010; Feuerstein et al., 2007; Hamel et al., 2008; Van Montfoort et al., 2008; Zhang et al., 2005). However, in the majority of these studies, they did not consider the possibility that CC gene expression profile might vary according to the stages of oocyte nuclear maturation and thus were focused mostly on a single specific phase of oocyte maturation, such as the MII stage (Feuerstein et al., 2007).

IVF is a powerful and widely used technique for the treatment of infertility. In this procedure, human eggs are retrieved and mixed with sperm in a culture dish to allow fertilization process. The embryos are then transferred to the uterus on day 2/3, when it has between 4 and 6-8 cells respectively or day 5 or 6 at blastocyst stage. This technique is used for women with, for example, damaged or absent Fallopian tubes, endometriosis, male factor infertility and unexplained infertility. However, the blastulation rate varies according the indications and male factor impact and this explain why implantation rate varies between 5% and 30%.

Under in vivo conception, the embryo reaches the uterus at a blastocyst stage of development. Accordingly, embryo coculture techniques, used successfully in animals, represent an effort to improve the culture media for embryos such that a greater proportion of embryos will reach the blastocyst stage for improving the implantation and pregnancy rates. In addition, if coculture results in a higher implantation rate, fewer embryos could be transferred at each cycle, resulting in a decreased incidence of multiple pregnancies. A variety of coculture techniques have been therefore investigated, involving the use of feeder cell layers derived from a range of tissues, including the use of human reproductive tissues (i.e., endometrium) and the coculture with cumulus cells (OMAR Farouk and Vlad, 2008; Quinn and Margalit, 1996 and EP0340934). However, no standardized method of growing an embryo to a blastocyst stage of development and no standardized method for coculture of embryo with cumulus cells for increasing the blastulation rate has emerged and the optimal system for preimplantation human embryo culture has not yet been determined.

SUMMARY OF THE INVENTION

The present invention relates to a method for determining whether a cumulus cell is mature or immature cumulus cell.

The present invention also relates to mature cumulus cells, immortalized mature cumulus cells, populations of mature cumulus cells and mature cumulus cell lines.

The present invention also relates to a novel human embryo co-culture system to improve human embryo growth in vitro and, consequently, increase pregnancy rates in infertile women undergoing IVF or ICSI treatment.

The present invention also relates to a method for selecting an oocyte that has a high probability to give rise upon fertilization to an embryo that will reach the blastocyst stage.

DETAILED DESCRIPTION OF THE INVENTION

The inventors have determined as set of 25 genes that are differentially expressed in human mature and immature cumulus cells.

The inventors indeed demonstrated that genes expression profile of cumulus cells that surround oocyte correlated to their developmental stages and that developmental stage of cumulus cells is correlated itself with blastulation rate, allowing the identification of a specific expression signature of oocyte developing toward blastocyst stage. Their results indicate that analysis of cumulus cells surrounding the oocyte is a non-invasive approach to predict blastulation rate for embryo selection.

All the genes pertaining to the invention are known per se, and are listed in the below Tables A. Tables A present the set of genes whose expression profile has been shown to be informative for determining whether a human cumulus cell is mature or immature.

TABLE A set of predictive genes whose overexpressions are indicative of mature cumulus cell

| Gene Symbol | Gene name | Probeset |
|---|---|---|
| C14orf4 | chromosome 14 open reading frame 4 | 223474_at |
| PTGES | prostaglandin E synthase | 210367_s_at |
| BRD3 | bromodomain containing 3 | 203825_at |
| UBR3 | ubiquitin protein ligase E3 component n-recognin 3 (putative) | 230029_x_at |
| COX17 | COX17 cytochrome c oxidase assembly homolog (S. cerevisiae) | 203880_at |
| C5orf25 | chromosome 5 open reading frame 25 | 228805_at |
| CHCHD1 | coiled-coil-helix-coiled-coil-helix domain containing 1 | 226896_at |
| PLEKHA5 | pleckstrin homology domain containing, family A member 5 | 220952_s_at |
| AOC2 | amine oxidase, copper containing 2 (retina-specific) | 207064_s_at |
| PWWP2A | PWWP domain containing 2A | 226720_at |
| ID2 | inhibitor of DNA binding 2, dominant negative helix-loop-helix protein | 201566_x_at |

TABLE B set of predictive genes whose overexpressions
are indicative of immature cumulus cell

| Gene Symbol | Gene name | Probeset |
|---|---|---|
| SLC38A2 | solute carrier family 38, member 2 | 220924_s_at |
| YTHDF2 | YTH domain family, member 2 | 222430_s_at |
| SUMF1 | sulfatase modifying factor 1 | 226850_at |
| EEF1A1 | eukaryotic translation elongation factor 1 alpha 1 | 213614_x_at |
| QKI | quaking homolog, KH domain RNA binding (mouse) | 212265_at |
| F2RL1 | coagulation factor II (thrombin) receptor-like 1 | 213506_at |
| ANKRD57 | ankyrin repeat domain 57 | 219496_at |
| THBS1 | thrombospondin 1 | 201109_s_at |
| CBX3 | chromobox homolog 3 (HP1 gamma homolog, Drosophila) | 201091_s_at |
| LIMS1 | LIM and senescent cell antigen-like domains 1 | 207198_s_at |
| RAI14 | retinoic acid induced 14 | 202052_s_at |
| TET3 | tet oncogene family member 3 | 235542_at |
| EXT1 | exostoses (multiple) 1 | 201995_at |
| PTGER2 | prostaglandin E receptor 2 (subtype EP2), 53 kDa | 206631_at |

An object of the invention relates to a method for determining whether a cumulus cell is a mature cumulus cell or an immature cumulus cell, comprising a step of measuring in said cumulus cell the expression level of at least one gene selected from Table A and at least one gene selected from Table B, wherein the overexpression of at least one gene selected from Table A is indicative that said cumulus cell is a mature cumulus cell and the overexpression of the at least one gene from Table B is indicative that cumulus cell is an immature cumulus cell.

The term "cumulus cell" refers to a cell comprised in a mass of cells that surrounds an oocyte. These cells are believed to be involved in providing an oocyte some of its nutritional, energy and or other requirements that are necessary to yield a viable embryo upon fertilization. Human cumulus cells (hCCs) are somatic cells found closely associated with the developing oocyte in the ovarian follicle. hCCs are stimulated to grow, differentiate and luteinize by endocrine, paracrine and autocrine factors. The major functions of hCCs include the production of steroids, as well as a myriad of growth factors to interact with the oocyte during its development within the ovarian follicle. However, after ovulation, the hCCs produce progesterone that may maintain a potential pregnancy.

Herein, the oocytes are classified into three categories based on nuclear status as disclosed in Feuerstein et al., 2007:
(i) immature oocyte at the germinal vesicle (GV) stage,
(ii) immature oocyte without first polar body or GV, arbitrarily called metaphase I (MI) and
(iii) mature oocyte with the first polar body (metaphase II, MII).

These categories correspond to three different developmental stages of oocytes.

The inventors have studied the gene expression profile of the cumulus cells surrounding oocytes of these three categories.

First, the inventors have studied the gene expression profile of a large population of cumulus cells surrounding oocytes MII.

Among this large population, a majority of cumulus cells surrounding oocytes MII has been shown to exhibit a specific gene expression profile. These cumulus cells are called herein cumulus cells MII ($CC_{MII}$) or mature cumulus cells or "competent" cumulus cells.

Then, in the same way, the inventors have studied the gene expression profile of a large population of cumulus cells surrounding oocytes MI and normal oocytes GV. For each of these two categories of cumulus cells, there is a majority of cumulus cells that exhibits a specific gene expression profile.

Cumulus cells exhibiting the majority gene expression profile of CC surrounding oocytes MI are called herein cumulus cells MI ($CC_{MI}$) and the cumulus cells exhibiting the majority gene expression profile of CC surrounding oocytes GV are called herein cumulus cell GV ($CC_{GV}$). Cumulus cells that are $CC_{MI}$ or $CC_{GV}$ are called herein immature cumulus cells or non competent cumulus cells.

Further, the inventors have studied the gene expression profile of individual cumulus cells surrounding different oocytes MII.

They have found that oocytes MII may be surrounded by $CC_{MII}$, $CC_{MI}$ or $CC_{GV}$ and that oocytes MII surrounded by mature cumulus ($CC_{MII}$)—that is the majority population—exhibit, upon fertilization, a higher rate of blastulation than oocytes MII surrounded by immature cumulus cells i.e. $CC_{MI}$ or $CC_{GV}$.

Thus, even if an oocyte is at the developmental stage needed to develop, upon fertilization, into a blastocyste, if it is surrounded by immature cumulus cells the blastulation rate will be low.

In a previous study disclosed in WO2010/118991, the inventors had shown that, due to the bidirectional exchanges between cumulus cells and oocytes, cumulus cells are an indicator of the competence of oocyte. Thus, a competent oocyte (i.e. an oocyte being able to produce, upon fertilization, a viable embryo with a high implantation rate leading to pregnancy) may be selected by measuring the gene expression profile of the cumulus cells surrounding said oocyte.

In the present invention, the inventors have shown that in addition to the competence of oocyte per se and to its developmental stage, the developmental stage of cumulus cells that surround oocyte is an additional factor for the development of a fertilized oocyte into an embryo.

Thus, mature cumulus cells are one category of CC, by opposition to immature cumulus cells, that are at a specific developmental stage. Such mature CC, when they surround an oocyte MII, increase the probability of said oocyte giving rise to an embryo that will reach the blastocyst stage upon fertilization.

Thus, mature cumulus cells, also called herein $CC_{MII}$, are cumulus cells at a developmental stage that increase the probability of said oocyte giving rise to an embryo that will reach the blastocyst stage upon fertilization.

The term "embryo" refers to a fertilized oocyte or zygote. Said fertilization may intervene under a classical in vitro fertilization (cIVF) or under an intracytoplasmic sperm injection (ICSI) procedure. The term "classical in vitro fertilization" or "cIVF" refers to a process by which oocytes are fertilised by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization, especially that associated with sperm donation.

As used herein, the term "blastocyst" refers to the structure formed in the early embryogenesis of mammals, after the formation of the morula. It possesses an inner cell mass (ICM), or embryoblast, which subsequently forms the embryo, and an outer layer of cells, or trophoblast, which later forms the placenta. The trophoblast surrounds the inner cell mass and a fluid-filled blastocyst cavity known as the blastocoele. The human blastocyst comprises 70-100 cells. Blastocyst formation begins at day 5 after fertilization in humans when the blastocoele opens up in the morula.

According to the invention, the oocyte may result from a natural cycle, a modified natural cycle or a stimulated cycle for cIVF or ICSI. The term "natural cycle" refers to the natural cycle by which the female or woman produces an oocyte. The term "modified natural cycle" refers to the process by which, the female or woman produces an oocyte or two under a mild ovarian stimulation with GnRH antagonists associated with recombinant FSH or hMG. The term "stimulated cycle" refers to the process by which a female or a woman produces one ore more oocytes under stimulation with GnRH agonists or antagonists associated with recombinant FSH or hMG.

As used herein, the term "overexpression of a gene" has its general meaning in the art and refers to a higher level of expression of a nucleic acid (e.g., mRNA) or protein relative to a reference level.

According to the invention the reference levels may be the expression levels that have been previously determined for cumulus cells GV, MI or MII. The term "overexpression" refers to at least 2× higher gene expression level than the reference level, preferably at least 5× higher than the reference level and preferably at least 10× higher than the reference level. Typically, for determining whether a cumulus cell is a cumulus cell MII the expression levels of the genes of Table A are compared to the reference levels that have been previously determined for cumulus cell GV or MI. Inversely, for determining whether a cumulus cell is GV or MI the expression levels of the genes of Table B are compared to the reference levels that have been previously determined for cumulus cell MII.

The present invention also relates to a method for determining whether a cumulus cell is a mature cumulus cell or an immature cumulus, comprising a step of measuring in said cumulus cell the expression level of at least one gene selected from the Table A or at least one gene selected from the Table B, wherein the overexpression of the at least one gene selected from Table A is indicative that said cumulus cell is a mature cumulus cell and the overexpression of the at least one gene selected from Table B is indicative that said cumulus cell is an immature cumulus cell.

The present invention also relates to a method for determining whether a cumulus cell is a mature cumulus cell or an immature cumulus cell, comprising a step of measuring in said cumulus cell the expression level of at least one gene selected from the Table A, wherein the overexpression of the gene selected from Table A is indicative that said cumulus cell is a mature cumulus cell.

The present invention also relates to a method for determining whether a cumulus cell is a mature cumulus cell or an immature cumulus cell, comprising a step of measuring in said cumulus cell the expression level of at least one gene selected from the Table B, wherein the overexpression of the gene selected from Table B is indicative that said cumulus cell is an immature cumulus cell.

Overexpression of one or more genes selected from Table A is indicative that said cumulus cell is mature. Overexpression of one or more genes selected from Table B is indicative that said cumulus cell is immature.

Said one or more genes may be selected for example from Table A alone or Table B alone.

Typically, 1 to 11 genes may be selected from Table A.
Typically, 1, 2, 3, 4, 5, 6, 7, 8, 9, 10 or 11 genes may be selected from Table A.
Typically, 1 to 14 genes may be selected from Table B.
Typically, 1, 2, 3, 4, 5, 6, 7, 8, 9, 10, 11, 12, 13 or 14 genes may be selected from Table B. Alternatively, said genes may be selected for example from Table A and B.
Typically, 1 to 11 genes may be selected from Table A, and 0 to 14 genes may be selected from Table B.
Typically, 0 to 11 genes may be selected from Table A, and 1 to 14 genes may be selected from Table B.

In a particular embodiment, the present invention relates to a method for determining whether a cumulus cell is a mature cumulus cell or an immature cumulus cell, comprising a step of measuring in said cumulus cell the expression level of the 25 genes of Table A and Table B, wherein the overexpression of the genes of Table A is indicative that said cumulus cell is a mature cumulus cell and the overexpression of the genes of Table B is indicative that cumulus cell is an immature cumulus cell.

The methods of the invention are applicable preferably to women but may be applicable to other mammals (e.g., primates, dogs, cats, pigs, cows, mouse . . . ).

The methods of the invention are particularly suitable for assessing the efficacy of an in vitro fertilization treatment. Accordingly the invention also relates to a method for assessing the efficacy of a controlled ovarian hyperstimulation (COS) protocol in a female subject comprising:

i) providing from said female subject at least one oocyte with its cumulus cells;
ii) determining by the method of the invention whether said cumulus cells are mature cumulus cells.

Then after such a method, the embryologist may select the oocytes surrounded with mature cumulus cells and in vitro fertilized them through a classical in vitro fertilization (cIVF) protocol or under an intracytoplasmic sperm injection (ICSI) protocol.

A further object of the invention relates to a method for monitoring the efficacy of a controlled ovarian hyperstimulation (COS) protocol comprising:

i) isolating from said woman at least one oocyte with its cumulus cells under natural, modified or stimulated cycles;
ii) determining by the method of the invention whether said cumulus cell is a mature cumulus cells;
iii) and monitoring the efficacy of COS treatment based on whether it results in an oocyte that is surrounded by mature cumulus cells.

The COS treatment may be based on at least one active ingredient selected from the group consisting of GnRH agonists or antagonists associated with recombinant FSH or hMG.

The present invention also relates to a method for selecting an oocyte that has a high probability to give rise upon fertilization to an embryo that will reach the blastocyst stage comprising the steps consisting of i) providing a plurality of oocytes, ii) isolating at least one cumulus cell surrounding said oocytes, iii) determining whether said at least one cumulus cell of step ii) is mature according to the method of the invention and iv) selecting the oocytes that are surrounded by mature cumulus cells.

Determination of the expression level of the genes as above described in Tables A and Table B can be performed by a variety of techniques. Generally, the expression level as determined is a relative expression level.

More preferably, the determination comprises contacting the sample with selective reagents such as probes, primers or ligands, and thereby detecting the presence, or measuring the amount, of polypeptide or nucleic acids of interest originally in the sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In a preferred embodiment, the expression level may be determined by determining the quantity of mRNA.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from cumulus cells and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (Hoheisel, 2006).

In this context, the invention further provides a DNA chip comprising a solid support which carries nucleic acids that are specific to the genes listed in table A.

Other methods for determining the expression level of said genes include the determination of the quantity of proteins encoded by said genes.

Such methods comprise contacting the sample with a binding partner capable of selectively interacting with a marker protein present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with an antibody against the protein to be tested. A biological sample containing or suspected of containing the marker protein is then added to the coated wells. After a period of incubation sufficient to allow the formation of antibody-antigen complexes, the plate (s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Alternatively an immunohistochemistry (IHC) method may be preferred. IHC specifically provides a method of detecting targets in a sample or tissue specimen in situ. The overall cellular integrity of the sample is maintained in IHC, thus allowing detection of both the presence and location of the targets of interest. Typically a sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan).

In particular embodiment, a tissue section (e.g. a sample comprising cumulus cells) may be mounted on a slide or other support after incubation with antibodies directed against the proteins encoded by the genes of interest. Then, microscopic inspections in the sample mounted on a suitable solid support may be performed. For the production of photomicrographs, sections comprising samples may be mounted on a glass slide or other planar support, to highlight by selective staining the presence of the proteins of interest.

Therefore IHC samples may include, for instance: (a) preparations comprising cumulus cells (b) fixed and embedded said cells and (c) detecting the proteins of interest in said cells samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

The invention also relates to a kit for performing the methods as above described, wherein said kit comprises means for measuring the expression level of the genes of Tables A and/or the expression level of the genes of Tables B.

The present invention also relates to a cumulus cell that has been determined as a mature cumulus cell by the method of the present invention. Accordingly said cumulus cell overexpresses at least one gene of Table A and preferably does not express a gene from Table B, and even more preferably overexpresses all genes of Table A.

The present invention also relates to a population of cumulus cells comprising at least 70% of mature cumulus cells determined by the method of the present invention.

Accordingly at least 70% of cumulus cells of such population overexpress at least one gene of Table A and preferably do not express a gene from Table B, and even more preferably overexpresses all genes of Table A.

Typically, the population of cumulus cells of the invention may comprise 70%, 80%, 90%, 95% or 99% of mature cumulus cells.

In a particular embodiment, the present invention relates to an immortalized mature cumulus cell or population of cumulus cells of the invention. Methods for immortalizing cells are well known in the art. For example, the immortalization of human cumulus cells can be performed via sequential lentiviral transduction of hTERT and SV40 large T antigen into a primary culture of human cumulus cells (Jiang et al., 2010; Liu et al., 2010; Voglauer et al., 2005).

In a particular embodiment, the present invention relates to a mature cumulus cell line.

Mature cumulus cells ("MCCs") may be useful in methods for growing embryos. The idea is that these cells will stimulate early embryos development by adding growth factors, or some other beneficial effect. MCCs may therefore use in IVF program, is that of culturing embryos to the blastocyst stage and then performing blastocyst transfer on day 5 or day 6. This allows increasing of blastulation rate and selection of best embryo that will be able to survive through the early cleavage stages of the first week of development. It is generally very difficult to get good numbers of high quality blastocysts when culturing in simples culture media. Accordingly, the present invention relates to a method for in vitro coculture of human embryo on human mature cumulus cells (MCCs).

Accordingly a further aspect of the present invention relates to a method of growing an embryo to a blastocyst stage of development comprising the step of coculturing said embryo in the presence of a population of mature cumulus cells according to the invention.

In one embodiment, the method of growing an embryo to a blastocyst stage may further comprise the steps of determining, according to the invention, from a population of cumulus cells which cumulus cells are mature cumulus cells and selecting the mature cumulus cells. The embryo is grown to a blastocyst stage prior to implantation.

In a particular embodiment, the mature cumulus cells are derived from a mature cumulus cell line.

Typically the embryo may result from an oocyte that was surrounded by mature cumulus cells or not. The method may be thus implemented with any source of oocytes.

The present invention also relates to a method according to the invention wherein said embryo was generated in vitro by any of the techniques selected from the group consisting of in vitro fertilization (IVF), including IVF performed by simple mixing of oocyte and sperm or by intracytoplasmic injection of sperm into an oocyte, and nuclear transfer.

The present invention also relates to a method of growing an embryo to a blastocyst stage of development, said method comprising a step of coculturing said embryo on a cell culture surface coated with a layer of mature cumulus cells according to the invention.

The term "cell culture surface" or "cell culture matrix" refers to every type of surface or matrix suitable for cell culture. The term "cell culture surface" includes but is not limited to tissue culture plate, dish, well or bottle. In a particular embodiment, the culture surface is plastic surface of the culture plate, dish, well or bottle. The cell culture surface is to be compatible with the coating of mature cumulus cells. According to an embodiment of the invention, the cell culture surface is selected in the manner that mature cumulus cells may naturally adhere on it. Various materials of cell culture surface may be selected. Examples of such materials include but are not limited to tissue culture dishes or dishes coated with collagen.

Typically, to obtain a layer of mature cumulus cells on a cell culture surface, the mature cumulus cells are first coated on the cell culture surface with a culture medium containing collagen. After a sufficient time for allowing adhesion of mature cumulus cell on the cell culture surface, the culture medium containing collagen is removed and replace by a medium that allows expansion of said mature cumulus cell.

The present invention also relates to a method according to the invention wherein the mature cumulus cells are previously treated to stop their proliferation before to in be in contact with the embryo. Therefore, the mature cumulus cells are inactivated by gamma irradiation or with a cell cycle blocking agent.

In accordance with the present invention, the culture conditions are also important for growing the embryo to a blastocyst stage of development. During culturing, variables such as temperature and CO2 levels can be controlled to maximize the growing of the embryo. For example, the optimum temperature for the development of an embryo is from about 32° C. and about 40° C., preferably from about 35° C. and 39° C., with a temperature of 37° C. being even more preferred. The optimum CO2 levels in the culturing environment for the development of an embryo is from about 1% CO2 to about 10% CO2, more preferably from about 3% CO2 to about 8% CO2, and even more preferably about 5% CO2.

Suitable media for growing embryos are well known in the art. For example, culture media are now available that allow embryos to progress to blastocysts at rates comparable with those occurring within the uterus (Summers and Biggers, 2003) raising the hope that such embryos will be free of the epigenetic marks introduced as a result of the stress of in vitro culture. Many of these media are based rather loosely on the concentrations of ions, amino acids, and sugars found in the reproductive tract of the female at the time of egg release, fertilization, and development (Gardner and Lane, 1998). Typically, culture media containing a phosphate buffer or Hepes organic buffer are used for procedures that involve handling of gametes outside of the incubator, flushing of follicles and micromanipulation. Most culture media utilize a bicarbonate/CO2 buffer system to keep PH in the range of 7.2-7.4. The osmolarity of the culture medium must be in the range of 275-290 mosmol/kg. Embryos could also be cultured under paraffin oil, which prevents evaporation of the medium preserving a constant osmolarity. The oil also minimizes fluctuations of pH and temperature when embryos are taken out of the incubator for microscopic assessment. Paraffin oil can be toxic to gametes and embryos; therefore, batches of oil must be screened and tested on mouse embryos before use in culture of human embryos.

The medium is composed of 99% water. Purity of the water is crucial, and is achieved by ultrafiltration.

Culture medium also contains a protein source, such as albumin or synthetic serum that are added in concentrations of 5 to 20% (w/v or v/v, respectively). As source of salt is also added to the medium such as NaCl, KCl, $KH_2PO_4$, $CaCl_2 2H_2O$, $MgSO_4 7H_2O$, or $NaHCO_3$. Culture medium also contains a carbohydrates source, since carbohydrates are present in the female reproductive tract. Together with the amino acids they are the main energy source for the embryo. Culture media that support the development of zygotes up to 8-cells contain pyruvate and lactate. Some commercial media are glucose free, while others add a very low concentration of glucose to supply the needs of the sperm during conventional insemination. Media that support the development of 8-cell embryos up to the blastocyst stage contain pyruvate and lactate in low concentrations and a higher concentration of glucose. Supplement of the culture medium with amino acids is also necessary for embryo development. Media that support the development of zygotes up to 8-cells are supplemented with non essential amino acids such as proline, serine, alanine, aspargine, aspartate, glycine, and glutamate. Media that support the development of 8-cell embryos up to the blastocyst stage are supplemented with essential amino acids such as cystine, histadine, isolucine, leucine, lysine, methionine, valine, argentine, glutamine, phenylalanine, therionine, tryptophane. The culture medium may also contain vitamins.

The culture medium may also contain antibiotics. The majority of ART laboratories use indeed culture media containing antibiotics to minimize the risks of microbial growth. The most commonly used antibiotics being Penicillin (β-lactam Gram-positive bacteria disturbs cell wall integrity) and Streptomycin (Aminoglycoside Gram-negative bacteria disturbs protein synthesis).

Three examples of sequential media for embryo development are: G1/G2 (Gardner et al, 1998), Universal IVF Medium/MS, and PI/Blastocyst Medium. Interestingly, medium M3 is a modification of Ham's F-10 and F-12, while Blastocyst Medium is a modification of Ham's F-10). Media for culturing embryo are commercially available from Origio (Denmark), Vitrolife (Sweden), Sage Biopharma (USA), Irvine Scientific (USA).

Also provided in accordance with certain embodiments of the present invention, is a method of increasing the in vivo implantation potential of an in vitro fertilization embryo. "Implantation potential" is the ability of the embryos to implant in the uterus. This method includes carrying out one of the above-described embodiments for growing an embryo to a blastocyst stage of development, such that complete hatching of the embryo in culture is achieved or hatching is enhanced, compared to other IVF methods. In accordance with certain embodiments of this method, the blastocyst is then introduced into the uterus of a mammalian host, such than enhanced implantation of the embryo is achieved. In some embodiments, complete hatching of the embryo in vitro correlates with establishment of a viable pregnancy.

In some embodiments of the present invention, a method of increasing the live birth potential of an in vitro fertilized mammalian embryo is provided. "Live birth potential" refers to the ability of an embryo to yield a live birth. The method comprises growing an embryo to a blastocyst stage of development, as described above, such that enhanced hatching potential or complete hatching of the embryos in culture is achieved. The blastocyst is then transferred to the uterus of a mammalian host; and the embryo is allowed to implant and grow in vivo, such that the ability of the embryo to yield a live birth is enhanced relative to that of an embryo that is not cultured according to the invention.

The method of the invention is also particularly suitable for limiting multiple pregnancies because it can provides a higher implantation rate, as above described and therefore fewer embryos could be transferred at each cycle, resulting in a decreased incidence of multiple pregnancies.

A further aspect of the invention relates to a method of maintaining the undifferentiated state in culture of a population of pluripotent stem cells comprising the step of coculturing said population of pluripotent stems cells in presence of a population of mature cumulus cells according to the invention.

As used herein, the term "human pluripotent stem cell" refers to any human precursor cell that has the ability to form any adult cell. In a particular embodiment, human pluripotent stem cells include but are not limited to embryonic stem cells (hES cells) or human induced pluripotent stem cells (human iPS cells).

As used herein, the term "human embryonic stem cells" or "hES cells" or "hESC" refers to human precursor cells that have the ability to form any adult cell. hES cells are derived from fertilized embryos that are less than one week old. According to an embodiment of the invention, hES cells may be selected from any hES cell lines. Examples of hES cell lines include but are not limited to, SA-01, VUB-01, H1 (Thomson et al., 1998), and H9 (Amit et al., 2000). According to the invention hES cells are not previously cultured in the presence of LIF as described in the international patent application WO2002/097068. Moreover, according to the invention it shall be understood that hES cells are not previously differentiated in embryoid bodies.

As used herein, the term "human induced pluripotent stem cells" or "human iPS cells" or "human iPSCs" refers to a type of human pluripotent stem cell artificially derived from a human non-pluripotent cell (e.g. an adult somatic cell). Human induced pluripotent stem cells are identical to human embryonic stem cells in the ability to form any adult cell, but are not derived from an embryo. Typically, a human induced pluripotent stem cell may be obtained through the induced expression of Oct3/4, Sox2, Klf4, and c-Myc genes in any adult somatic cell (e.g. fibroblast). For example, human induced pluripotent stem cells may be obtained according to the protocol as described by Takahashi et al. (2007), by Yu et al. (2007) or else by any other protocol in which one or the other agents used for reprogramming cells in these original protocols are replaced by any gene or protein acting on or transferred to the somatic cells at the origin of the iPS lines. Basically, adult somatic cells are transfected with viral vectors, such as retroviruses, which comprises Oct3/4, Sox2, Klf4, and c-Myc genes. According to an embodiment of the invention human iPS cells may be selected from any human iPS cell lines. Examples of human iPS cell lines include but are not limited to clones 201B (Takahashi et al., 2007) and iPS (Foreskin or IMR90)-1-MCB-1 (Yu et al., 2007).

An embodiment of the invention relates to a method of maintaining the undifferentiated state in culture of a population of pluripotent stem cells, said method comprising a step of culturing said population of pluripotent stem cells on a cell culture surface coated with a layer of mature cumulus cells.

Said layer of mature cumulus cells may be obtained as described for the method of growing embryo to a blastocyst stage of development (see supra).

In accordance with the present invention, the culture conditions are also important in maintaining the undifferentiated state in culture of a population of pluripotent stem cell. During culturing, variables such as cell density, temperature and $CO_2$ levels can be controlled to maximize the development of populations of pluripotent stem cells. For example, the density of cells in a pluripotent stem cell culture can affect the spontaneous differentiation of said population. As such, the optimum cell density for the growth of a pluripotent stem cell population is from about 1 pluripotent stem cell to about 10,000 pluripotent stem cells per cm2, more preferably from about 1 pluripotent stem cell to about 2000 pluripotent stem cells per cm2, and even more preferably from about 100 to about 1000 pluripotent stem cells per cm2. In one embodiment, the pluripotent stem cells are cultured as a single cell suspension. The optimum temperature for the development of a pluripotent stem cell population is from about 32° C. and about 40° C., preferably from about 35° C. and 39° C., with a temperature of 37° C. being even more preferred. The optimum $CO_2$ levels in the culturing environment for the development of pluripotent stem cell populations is from about 1% $CO_2$ to about 10% $CO_2$, more preferably from about 3% $CO_2$ to about 8% $CO_2$, and even more preferably about 5% $CO_2$.

Suitable media for culturing pluripotent stem cells include Dulbeco's Modified Eagle Media (Invitrogen, Carlsbad, Calif.). The skilled artisan will appreciate that a wide range of media suitable for culturing pluripotent stem cells in vitro are available, e.g., Specialty Media (Millipore Corporation, Billerica, Mass.); Resgro™ (Millipore Corporation, Billerica, Mass.); StemXvivo (R&D Systems, Minneapolis, Minn.). The media may be supplemented with serum, e.g. fetal bovine serum, ES qualified serum (Invitrogen, Carlsbad, Calif.), antibiotics, e.g. Pen Strep (Invitrogen, Carlsbad, Calif.), non-essential amino acids (Invitrogen, Carlsbad, Calif.) and glutamine, e.g. Glutamax-1® (Invitrogen, Carlsbad, Calif.). Some ESC cultures may be further supplemented with leukemia inhibitory factor, e.g., Esgro® (Millipore Corporation, Billerida, Mass.).

The invention will be further illustrated by the following figures and examples. However, these examples and figures should not be interpreted in any way as limiting the scope of the present invention.

EXAMPLE 1

Figure 1:
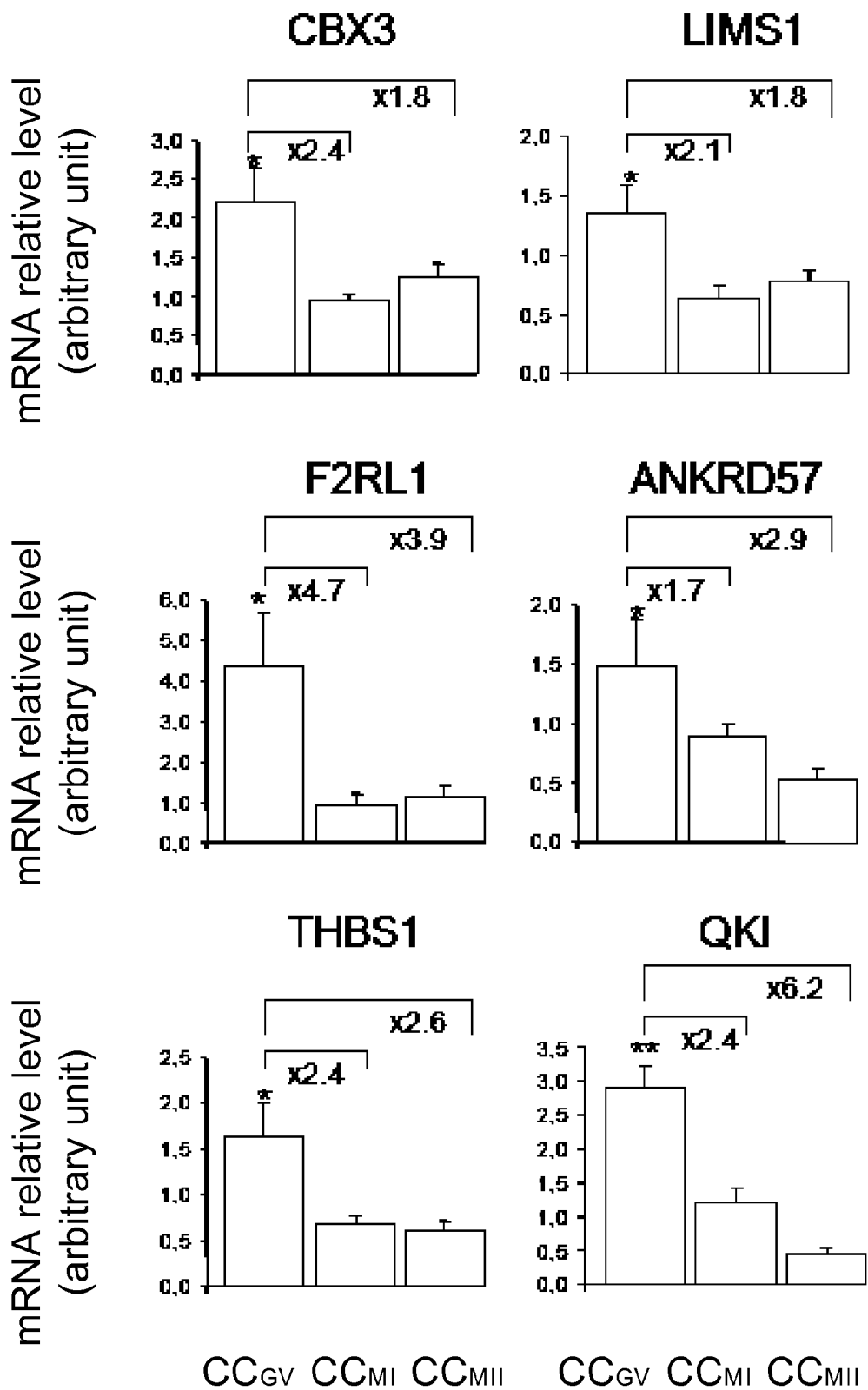
FIGS. 1A-C: Quantitative RT-PCR confirmation of the microarray data. Quantification of genes that were differentially expressed in CCs derived from oocytes at different stages of nuclear maturation. The signal intensity for each gene is shown on the y axis in arbitrary units determined by RT-qPCR analysis. 1A represents the expression levels of CBX3, LIMS1, F2RL1, ANKRD57, THBS1 and QKI; 1B represents the expression levels of SLC38A2, SUMF1 and YTHDF2; and 1C represents the expression levels of C14orf4, PTGES, COX17, C5orf25, UBR3 h and BRD3. *Indicates a significant difference of gene expression between CCs groups (**$p<0.01$, *$p<0.05$). Results were presented as the mean±SEM of the mRNA levels in each CC group.
Figure 1:
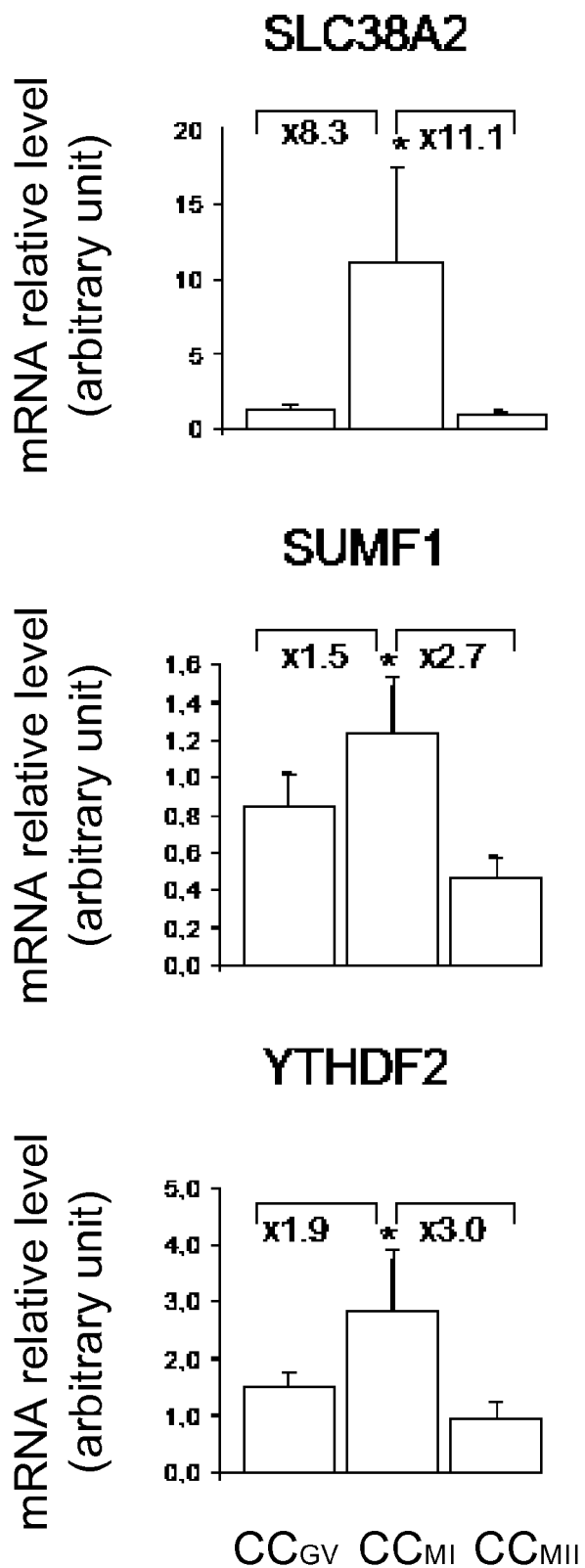
Figure 1:
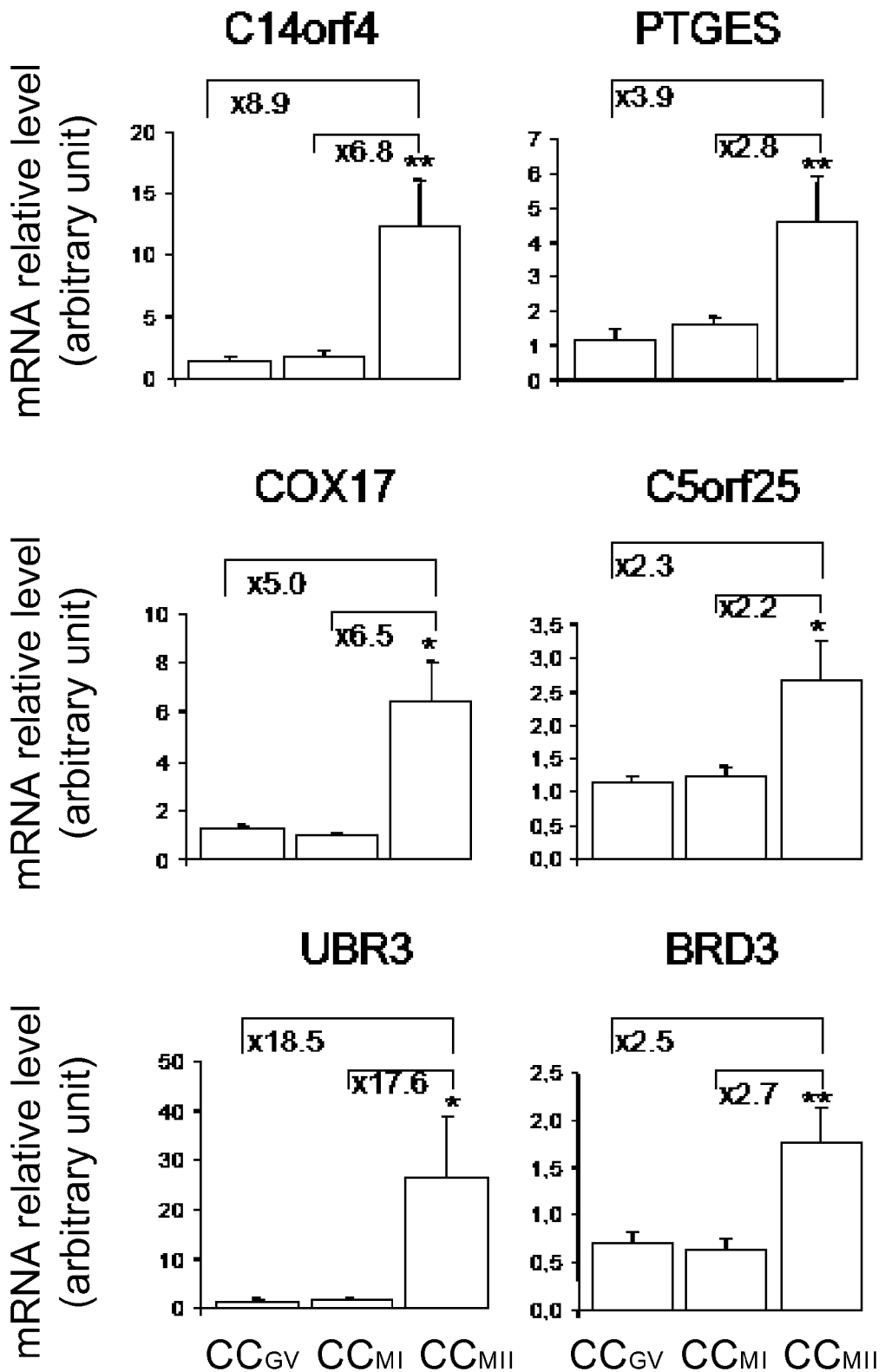

A Non-Invasive Test for Prediction of Blastulation Rate by Gene Expression Profile of Human Mature and Immature Cumulus Cells Methods:
Processing of Cumulus Cells:

Normal responder patients (age<36) referred to our center for intra-cytoplasmic sperm injection (ICSI) were included in this study. Patients were included after written informed consent and the project was approved by the Institute review board (IRB). Patients were stimulated with a combination of GnRH agonist or antagonist protocols with recombinant FSH or with HP hMG. COCs were recovered under ultrasound echo-guidance 36 h after human Chorionic Gonadotrophin (5 000 UI, hCG) administration. CCs were separated mechanically from the corresponding oocyte as previously described (Hamel et al., 2008). One to 3 CC samples per patient were randomly selected from the same CC cohort. A total of 111 CC samples obtained from 40 patients were used in this study.

For microarray analyses, 24 individual CC samples obtained from 16 patients were divided into three distinct groups according to oocyte nuclear maturation stage: samples derived from COC (i) at germinal vesicle ($CC_{GV}$) stage, (ii) metaphase I stage ($CC_{MI}$), and (iii) metaphase II stage ($CC_{MII}$). The differential gene expression profile in the three CC groups was investigated. For reverse-transcription quantitative polymerase chain reaction (RT-qPCR), 24 CC samples (8 samples for each stage of nuclear maturation) obtained from 19 patients were used. For testing reliability of the candidate genes, 63 CC samples derived from mature (MII) oocytes and obtained from 5 patients were analyzed by microarrays.

Complementary RNA Preparation and Microarray Hybridization:

Total RNA from CC samples was extracted using the RNeasy Micro Kit (Qiagen). RNA was quantified using a Nanodrop ND-1000 spectrophotometer (Nanodrop Technologies, Wilmington, Del., USA). RNA integrity and quality were evaluated with an Agilent 2100 Bioanalyzer (Agilent, Palo Alto, Calif., USA). RNA samples were stored at −80° C. until microarray analysis. The Affymetrix 3' IVT express protocol (ref 901229) was used to prepare cRNA (one-cycle amplification) with a starting concentration of 100 ng of total RNA. First-strand DNA was synthesized using an oligo-dT primer that incorporates a T7 promoter sequence. cDNA was then amplified by in vitro transcription (IVT) with T7 RNA polymerase. During RNA amplification (aRNA) a biotinylated nucleotide analog was incorporated to be used as a label for the message. After fragmentation, the labeled anti-sense aRNA was hybridized to HG-U133 Plus 2.0 arrays (Affymetrix™) as described previously (Tusher et al., 2001).

Data Processing:

Scanned GeneChip images were processed using the Affymetrix GCOS 1.4 software. Microarray data were analyzed using the Affymetrix Expression Console™ software and normalization was performed with the MAS5.0 algorithm to obtain the signal intensity and the detection call (present, marginal, or absent) for each probe set. This algorithm determines whether a gene is expressed with a defined confidence level or not ("detection call"). This "call" can either be "present" (when the perfect match probes are significantly more hybridized than the mismatch probes, FDR <0.04), "marginal" (for FDR ≥0.04 and ≤0.06) or "absent" (FDR >0.06). FDR, false discovery rate.

Microarray Data Analysis:

To compare the gene expression profile of the 24 CC samples according to the oocyte maturation stage, we first filtered the samples based on the "detection call" (i.e., absent/present). Probe sets were used when they were present in at least 7 samples out of 24. A second filter that uses the variation coefficient (40%) between all the samples was also applied. The coefficient of variation is the ratio, expressed in percentage, between standard deviation (SD) and mean of signal intensity of each probe set. To compare the gene expression profile of the 24 CC samples according to the oocyte maturation stage, we first filtered the samples based on the "detection call" (i.e., absent/present). Probe sets were used when they were present in at least 7 samples out of 24. A second filter that uses the variation coefficient (40%) between all the samples was also applied. The coefficient of variation is the ratio, expressed in percentage, between standard deviation (SD) and mean of signal intensity of each probe set. To compare groups of CCs at different stages of oocyte nuclear maturation, a Significance Analysis of Microarrays-Multi-class (SAM-M) (Eisen et al., 1998) was performed. This algorithm provides the score values and a false discovery rate (FDR) confidence percentage based on data permutation. SAM-M allowed the identification of genes whose expression varied significantly among the $CC_{GV}$, $CC_{MI}$ and $CC_{MII}$ groups.

The SAM-M results were used to perform a supervised hierarchical clustering, based on the expression level of the probe sets (multiclass gene set), and the cluster was visualized using the Tree View software (Adriaenssens et al., 2009). The Ingenuity Pathways Analysis (IPA) system (Ingenuity Systems, Redwood City, Calif., USA) was used to identify networks related to the 25 genes that were differentially expressed among the three CC groups.

Reverse-Transcription Quantitative Polymerase Chain Reaction (RT-qPCR):

We performed RT-qPCR to validate the expression of the candidate genes using the Superscript First Strand Synthesis System (Invitrogen) according to the manufacturer's recommendation. An independent cohort of CC samples was used for the validation. First strand cDNA was generated starting from 300 ng of total RNA from each sample and used (dilution 1:10) to assess gene expression by qPCR in 384-wells plates on a Light Cycler 480

(Roche). Each well contained a total of 8 µL of Master SYBR green (Roche) mix and 2 µL of diluted DNA with a final concentration of 1.625 µM of each primers (Sigma). To check reproducibility, each RT-qPCR reaction was carried out in duplicate, and water was used as a negative control. The amplification was a 45-cycle run with annealing temperature at 60° C. PCR products were monitored with the SYBR green probe. Details of the primers used are reported in Supplementary Table 1. To normalize the expression level among the samples, we used Glyceraldehyde 3-Phosphate Dehydrogenase (GAPDH) because its expression was stable in the three CC groups. PCR efficiency was evaluated using serial dilutions of a standard scale of cDNA. The cycle number ("Ct" for cycle threshold) value was used to calculate the relative amount of mRNA transcripts. We used the following formula to analyze the qRT-PCR data: $E_{tested\ primer}^{\Delta Ct}/E_{GAPDH}^{\Delta Ct}$ ($E=10^{-1/slope}$), where $\Delta Ct=Ct$ Control-Ct unknown and control=one CC sample. As internal control of the three groups a $CC_{GV}$ sample was chosen.

Statistical Analysis:

The data obtained by RT-qPCR was analyzed with the GraphPad Instat software and the Kruskal-Wallis non-parametric test. Difference among the three groups were considered significant when the p-value was <0.05.

Results

Identification of Sets of Genes Over-Expressed in CCs According to Each Stage of Oocyte Nuclear Maturity:

Using SAM-M, we identified a total of 25 genes (multiclass gene set) with a FDR≤3.30 that significantly distinguished the three groups. These 25 genes were differentially over-expressed according to the stage of nuclear maturity of the associated oocyte. More precisely, 10, 4 and 11 genes were specifically over-expressed in the $CC_{GV}$, $CC_{MI}$ and $CC_{MII}$ groups respectively (Table I). The number of genes that are specific for a given group of CCs indicates that there is a significant variation across the three groups of CCs as demonstrated also by the supervised hierarchical clustering which shows a clear segregation of the CC samples based on this list of 25 genes.

TABLE I genes specifically over-expressed in the $CC_{GV}$, $CC_{MI}$ and $CC_{MII}$ groups

| Gene Symbol | Gene name | Probeset |
| --- | --- | --- |
| Genes over-expressed in the $CC_{MII}$ | | |
| C14orf4 | chromosome 14 open reading frame 4 | 223474_at |
| PTGES | prostaglandin E synthase | 210367_s_at |
| BRD3 | bromodomain containing 3 | 203825_at |

TABLE I-continued genes specifically over-expressed
in the CC$_{GV}$, CC$_{MI}$ and CC$_{MII}$ groups

| Gene Symbol | Gene name | Probeset |
|---|---|---|
| UBR3 | ubiquitin protein ligase E3 component n-recognin 3 (putative) | 230029_x_at |
| COX17 | COX17 cytochrome c oxidase assembly homolog (S. cerevisiae) | 203880_at |
| C5orf25 | chromosome 5 open reading frame 25 | 228805_at |
| CHCHD1 | coiled-coil-helix-coiled-coil-helix domain containing 1 | 226896_at |
| PLEKHA5 | pleckstrin homology domain containing, family A member 5 | 220952_s_at |
| AOC2 | amine oxidase, copper containing 2 (retina-specific) | 207064_s_at |
| PWWP2A | PWWP domain containing 2A | 226720_at |
| ID2 | inhibitor of DNA binding 2, dominant negative helix-loop-helix protein | 201566_x_at |
| Genes over-expressed in the CC$_{MI}$ | | |
| SLC38A2 | solute carrier family 38, member 2 | 220924_s_at |
| YTHDF2 | YTH domain family, member 2 | 222430_s_at |
| SUMF1 | sulfatase modifying factor 1 | 226850_at |
| EEF1A1 | eukaryotic translation elongation factor 1 alpha 1 | 213614_x_at |
| Genes over-expressed in the CC$_{GV}$ | | |
| QKI | quaking homolog, KH domain RNA binding (mouse) | 212265_at |
| F2RL1 | coagulation factor II (thrombin) receptor-like 1 | 213506_at |
| ANKRD57 | ankyrin repeat domain 57 | 219496_at |
| THBS1 | thrombospondin 1 | 201109_s_at |
| CBX3 | chromobox homolog 3 (HP1 gamma homolog, Drosophila) | 201091_s_at |
| LIMS1 | LIM and senescent cell antigen-like domains 1 | 207198_s_at |
| RAI14 | retinoic acid induced 14 | 202052_s_at |
| TET3 | tet oncogene family member 3 | 235542_at |
| EXT1 | exostoses (multiple) 1 | 201995_at |
| PTGER2 | prostaglandin E receptor 2 (subtype EP2), 53 kDa | 206631_at |

Ten genes were over-expressed in the CC$_{GV}$ group: a Prostaglandin receptor (PTGER2), a G-protein coupled receptor (F2RL1), a structural binding protein (RAI14), two nuclear components (CBX3 and QKI), genes involved in adhesion (THBS1, LIMS1), protein-protein interaction (ANKRD57) or associated with Heparan Sulfate biosynthesis, a member of the TET family (TET3) and EXT1. Four genes were found to be over-expressed in the CC$_{MI}$ group: an amino acid transporter (SLC38A2), a signal transducer (YTHDF1) containing an Alu-rich domain, a Sulfatase activator (SUMF1) and an elongation factor (EEF1A1). In CC$_{MII}$ samples, we found 11 over-expressed genes: four transcription factors (ID2, CHCHD1, UBR3, BRD3), two genes involved in transcription regulation (C14orf4 and AOC2), as well as PLEKHA5, PTGES, and COX17 (involved in Prostaglandin biosynthesis), PWWP2A and C5orf25.

The 25 genes were then screened by RT-qPCR using an independent cohort of CC samples to strongly validate the microarray results. Fifteen genes were statistically validated as being differentially expressed in the three groups (FIGS. 1A, 1B and 1C).

Mature MII Oocytes have Distinct Expression Patterns in their Surrounding CCs:

Microarray analysis was performed on an independent cohort of 63 CC samples from mature MII oocytes obtained from 5 patients to measure the relative abundance of the transcripts of interest genes in CCs. By checking the expression profile of the 15 validated CC genes (FIGS. 1A, 1B and 1C) using unsupervised hierarchical clustering, we found that 31, 24 and 45% of fertilized mature oocytes express CC$_{GV}$, CC$_{MI}$, and CC$_{MII}$ molecular signatures respectively.

This result demonstrated that mature MII oocyte can be surrounded by either CCs which corresponding to CC$_{GV}$ or CC$_{MI}$ or CC$_{MII}$ stages respectively. Indeed, the mature MII oocytes can be surrounded by distinct expression patterns. Although the notion of synchronized maturation during folliculogenesis between oocyte and CCs is well documented in animal models, it was not yet clearly demonstrated in humans (Russell and Robker, 2007). In the present study, we observed that less than 50% of mature oocytes were surrounded by CC$_{MII}$.

Mature Oocytes Surrounded by Either "Mature" or "Immature" CCs:

Among the 63 CC samples derived from mature (MII) oocytes, 53 were fertilized and included to assess embryo outcome. In order to test the reliability of the 15 validated gene list, we assessed the fertilization rate, cleavage of embryo on day 3 and blastocyst formation rate. Two groups were generated according to either the CC$_{MII}$ specific molecular signature or the CC$_{GV}$ and CC$_{MI}$ molecular signatures. Groups I and II were referred as "CC$_{MII}$" and "CC$_{GV-MI}$" signatures, respectively. The comparison between the 2 groups revealed no significant difference in fertilization rate and cleavage of embryo on day 3 (Table II). Interestingly, the t-test revealed a significant difference (p=0.04) for blastocyst formation between the group I and group II. Blastocyst formation rate was higher (70.8%) in group I compared to group II (17.2%). Thus, mature oocytes had mature CC with increased mature gene expression (CC$_{MII}$) and immature CC with increased immature gene expression (CC$_{GV-MI}$).

These results provide validation of our new model according to which that mature oocyte can be surrounded either by mature or immature cumulus cells. In a clinical perspective, we suggest that CCs screening at the mature oocyte stage using microarray or q-RT-PCR or immunofluorescence is likely to be an accurate tool for detecting mature CCs and may assist in identifying embryos' potential during IVF cycles (preferentially transferring embryos obtained from mature oocyte with mature CCs).

TABLE II

| | Mature CC | immature CC | P-value |
|---|---|---|---|
| Number of samples | 24 | 29 | |
| Fertilization rate (%) | 71 | 74 | NS |
| Embryo nbr on day 3 (>=6 cells) | 24 | 29 | NS |
| Blastocyst stage (%) | 70.8 | 17.2 | 0.04 |

EXAMPLE 2

Isolation of Human Cumulus Cells

Cumulus cells are obtained from consecutive patients with their informed consent. After examination of the cumulus mass appearance, the human cumulus cells (hCCs) are mechanically separated from the oocyte by using two needles. One needle placed on the hCCs layer to keep the oocyte in place and the other needle, is used to quickly cut off as much as possible of the cell layer, without touching the oocyte. Aspirate the cell with as little medium as possible and transfer these cells into the prepared medium.

EXAMPLE 3

Culture and Amplification of Human Mature Cumulus Cells (hMCCs)

In an initial experiment, hMCCs are cultured in Dulbecco's modified Eagle's medium (DMEM) with 10% fetal calf serum (FCS) and 10 ng/ml fibroblast growth factor (bFGF) and with gelatin (0.1%) coated plates. Using this cultivation protocol, hMCCs adhere to surface at 4 hrs after inoculation. Medium is replaced three times a week until confluence reaches 80%. Cells are passaged every 5-7 days enzymatically with 0.25% trypsin/EDTA. The MCC line are adapted to growth on a this condition (>12 passages).

Serum (FCS) is an undefined substance with multiple factors that might influence cell function and the reliance on animal products limits the clinical application. For this reason, cultivation protocols are optimized for long-term cultivation of hMCCs on animal free condition. We coat culture plates with HP01 medium containing human collagen I-III at 10 µg/cm$^2$ during two hours. We remove carefully the adhesion solution and replaced it by defined SPE-IV expansion medium (clinical grade human albumin, synthetic iron carrier, rh-insulin, nucleosides, L-glutamine, -monothioglycerol, synthetic lipids, alpha-MEM). This culture medium contains growth factors (rhIGF-I: 25 ng/ml and rh-b-FGF: 0.33 ng/ml). The cell concentration is fixed at 1.000 cells/cm$^2$. We change completely the medium four times a week until confluence reaches 70-80%.

The inventors have developed and analyzed a newly hMCCs line that contains chromosomal stability. These hMCCs line are adapted to growth on a human collagen substrate in animal free defined medium (>10 passages). This growth system reduces exposure of hMCCs to animal ingredients, thereby limiting the risk of pathogenic contamination.

EXAMPLE 4

Preparation of MCC Feeder Layer

Monolayer of hMCCs (passage 5) are cultured to confluency and treated with 10 µg/ml mitomycin-C for 2 h or by irradiation. Following treatments, cells are detached with Tryple and seeded onto culture dishes.

EXAMPLE 5

Human Embryonic Stem Cells (hESCs) Grew on the hMCCs Feeder Layer

The propagation and pluripotent characteristics of a human embryonic stem cell (hESC) line are studied in prolonged culture in on hMCCs. We reported that hESC cultured on hMCCs were indistinguishable by multiple criteria (morphology, pluripotency markers) from hESC cultured on a fibroblast feeder layer. We show that hESC grown on hCCs maintain markers of pluripotency, including expression of cell surface proteins (SSEA3, SSEA4, TRA-1-60, TRA-1-81). The morphology and molecular characteristics of the cells are similar as compared to the hESC cultured on fibroblast feeder cells.

In conclusion, the hMCCs support undifferentiated hESC growth. hESC lines readily adapt to these feeders and maintain the typical morphology of undifferentiated hESC cultures. The hESC also continue to express pluripotent markers, including TRA-1-60, SSEA3, SSEA-4, Tra-1-81 and CD24.

EXAMPLE 6

Global Gene Expression Analysis Validates hMCCs for "Embryo" Propagation

Genome-wide gene expression profiles of HFF feeder cells and hMCCs express 62% of gene expression similarity. The correlation coefficients among the two samples are high, with only a small number of genes showing statistically significant differential expression.

REFERENCES

Throughout this application, various references describe the state of the art to which this invention pertains. The disclosures of these references are hereby incorporated by reference into the present disclosure.

Adriaenssens T, Mazoyer C, Segers I, Wathlet S, Smitz J. Differences in collagen expression in cumulus cells after exposure to highly purified menotropin or recombinant follicle-stimulating hormone in a mouse follicle culture model. Biol Reprod 2009: 80(5):1015-25.

Adriaenssens T, Wathlet S, Segers I, Verheyen G, De Vos A, Van der Elst J, Coucke W, Devroey P, Smitz J. Cumulus cell gene expression is associated with oocyte developmental quality and influenced by patient and treatment characteristics. Hum Reprod 2010; 25:1259-1270.

Amit M, Carpenter M K, Inokuma M S, Chiu C P, Harris C P, Waknitz M A, Itskovitz-Eldor J, Thomson J A. Clonally derived human embryonic stem cell lines maintain pluripotency and proliferative potential for prolonged periods of culture. Dev Biol. 2000: 227(2):271-8.

Assou S, Haouzi D, Mahmoud K, Aouacheria A, Guillemin Y, Pantesco V, Rème T, Dechaud H, De Vos J, Hamamah S. A non-invasive test for assessing embryo potential by gene expression profiles of human cumulus cells: a proof of concept study. Mol Hum Reprod 2008; 14:711-719

Assou S, Haouzi D, De Vos J, Hamamah S. Human cumulus cells as biomarkers for embryo and pregnancy outcomes. Mol Hum Reprod 2010; 16:531-538.

Cha K Y, Chian R C. Maturation in vitro of immature human oocytes for clinical use. Hum Reprod Update 1998; 4:103-120. Review.

Eisen M B, Spellman P T, Brown P O, Botstein D. Cluster analysis and display of genome-wide expression patterns. Proc Natl Acad Sci USA 1998; 95:14863-14868.

Feuerstein P, Cadoret V, Dalbies-Tran R, Guerif F, Bidault R, Royere D. Gene expression in human cumulus cells: one approach to oocyte competence. Hum Reprod 2007; 22:3069-3077.

Gardner D K, Lane M. Culture of viable human blastocysts in defined sequential serum-free media. Hum Reprod. 1998: 13 (3):148-60.

Gardner D K, Schoolcraft W B, Wagley L, Schlenker T, Stevens J, Hesla J. A prospective randomized trial of blastocyst culture and transfer in in-vitro fertilization. Hum Reprod. 1998: 13(12):3434-40.

Goud P T, Goud A P, Qian C, Laverge H, Van der Elst J, De Sutter P, Dhont M. In-vitro maturation of human germinal vesicle stage oocytes: role of cumulus cells and epidermal growth factor in the culture medium. Hum Reprod 1998; 13:1638-1644.

Hamel M, Dufort I, Robert C, Gravel C, Leveille M C, Leader A, Sirard M A. Identification of differentially expressed markers in human follicular cells associated with competent oocytes. Hum Reprod 2008; 3:1118-1127.

Hoheisel J D. Microarray technology: beyond transcript profiling and genotype analysis. Nat Rev Genet. 2006: 7(3):200-10.

Jiang M, Min Y, Debusk L, Fernandez S, Strand D W, Hayward S W, Lin P C. Spontaneous immortalization of human dermal microvascular endothelial cells. World J Stem Cells. 2010: 26; 2(5):114-20.

Liu S, Hatton M P, Khandelwal P, Sullivan D A. Culture, immortalization, and characterization of human meibomian gland epithelial cells. Invest Ophthalmol V is Sci. 2010: 51(8):3993-4005.

Omar Farouk F N, Vlad M. In vitro development of mouse pronuclear embryos to blastocysts in sequential media with and without co-culture of autologous cumulus cells. J Reprod Dev. 2008: 54(5):385-90.

Quinn P, Margalit R. Beneficial effects of coculture with cumulus cells on blastocyst formation in a prospective trial with supernumerary human embryos. J Assist Reprod Genet. 1996: 13(1):9-14.

Russell D L, Robker R L. Molecular mechanisms of ovulation: co-ordination through the cumulus complex. Hum Reprod Update 2007; 13:289-312.

Salustri A, Yanagishita M, Hascall V C. Synthesis and accumulation of hyaluronic acid and proteoglycans in the mouse cumulus cell-oocyte complex during follicle-stimulating hormone-induced mucification. J Biol Chem 1989; 264:13840-13847.

Summers M C, Biggers J D. Chemically defined media and the culture of mammalian preimplantation embryos: historical perspective and current issues. Hum Reprod Update. 2003: 9(6):557-82.

Takahashi K, Tanabe K, Ohnuki M, Narita M, Ichisaka T, Tomoda K, Yamanaka S. Induction of pluripotent stem cells from adult human fibroblasts by defined factors. Cell. 2007: 30; 131(5):861-72.

Thomson J A, Itskovitz-Eldor J, Shapiro S S, Waknitz M A, Swiergiel J J, Marshall V S, Jones J M. Embryonic stem cell lines derived from human blastocysts. Science. 1998: 282(5391):1145-7.

Tusher V G, Tibshirani R, Chu G Significance analysis of microarrays applied to the ionizing radiation response. Proc Natl Acad Sci USA 2001: 98(9):5116-21.

Van Montfoort A P, Geraedts J P, Dumoulin J C, Stassen A P, Evers J L, Ayoubi T A. Differential gene expression in cumulus cells as a prognostic indicator of embryo viability: a microarray analysis. Mol Hum Reprod 2008; 14:157-168.

Voglauer R, Grillari J, Fortschegger K, Wieser M, Sterovsky T, Gunsberg P, Katinger H, Pfragner R. Establishment of human fibroma cell lines from a MEN1 patient by introduction of either hTERT or SV40 early region. Int J Oncol. 2005: 26(4):961-70.

Wang Q, Sun Q Y. Evaluation of oocyte quality: morphological, cellular and molecular predictors. Reprod Fertil Dev 2007; 19:1-12.

Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. Induced pluripotent stem cell lines derived from human somatic cells. Science. 2007: 21; 318(5858):1917-20.

Zhang X, Jafari N, Barnes R B, Confino E, Milad M, Kazer R R. Studies of gene expression in human cumulus cells indicate pentraxin 3 as a possible marker for oocyte quality. Fertil Steril 2005; 83:1169-1179.

The invention claimed is:

1. A method for implanting an embryo in a female undergoing in vitro fertilization, comprising the steps of:
    a) obtaining an oocyte with its cumulus cells from said female;
    b) measuring in one of said cumulus cells an expression level of:
        at least five genes selected from the Table A, and
        at least seven genes selected from the Table B,
    c) comparing:
        the expression level of said at least five genes selected from the Table A with control expression levels of said at least five genes in immature cumulus cells; and
        the expression level of said at least seven genes selected from the Table B with control expression levels of said at least seven genes in mature cumulus cells,
    wherein overexpression of the at least five genes selected from Table A compared to the control expression levels of said at least five genes is indicative that said cumulus cell is a mature cumulus cell, and
    overexpression of the at least seven genes selected from Table B compared to the control expression levels of said at least seven genes is indicative that said cumulus cell is an immature cumulus cell;
    d) fertilizing the oocyte obtained in step a) in vitro to generate an embryo when said cumulus cell is assessed as mature in step c) or when said cumulus cell is not assessed as immature in step c); and
    e) implanting said embryo in said female.

2. A method for implanting an embryo in a female undergoing in vitro fertilization, comprising the steps of:
    a) obtaining an oocyte with its cumulus cells from said female;
    b) measuring in one of said cumulus cells, the expression level of all the 25 genes of Table A and Table B
    c) comparing:
        the expression level of said genes selected from the Table A with control expression levels of said genes in immature cumulus cells; and
        the expression level of said genes selected from the Table B with control expression levels of said genes in mature cumulus cells,
    wherein overexpression of the genes selected from Table A compared to the control expression levels of said genes is indicative that said cumulus cell is a mature cumulus cell, and
    overexpression of the genes selected from Table B compared to the control expression levels of said genes is indicative that said cumulus cell is an immature cumulus cell;
    d) fertilizing the oocyte obtained in step a) in vitro to generate an embryo when said cumulus cell is assessed as mature in step c) or when said cumulus cell is not assessed as immature in step c); and
    e) implanting said embryo in said female.

* * * * *